US010188822B2

(12) United States Patent
Flanagan et al.

(10) Patent No.: US 10,188,822 B2
(45) Date of Patent: Jan. 29, 2019

(54) GAS DELIVERY DEVICE AND SYSTEM FOR USE IN MAGNETIC RESONANCE IMAGING

(71) Applicant: Mallinckrodt Hospital Products IP Limited, Dublin (IE)

(72) Inventors: Craig Flanagan, Belmar, NJ (US);
David Newman, Lebanon, NJ (US);
Jaron M. Acker, Madison, WI (US);
Craig R. Tolmie, Stoughton, WI (US);
Jim Potenziano, Binghamton, NY (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 777 days.

(21) Appl. No.: 14/657,548

(22) Filed: Mar. 13, 2015

(65) Prior Publication Data
US 2015/0258299 A1   Sep. 17, 2015

Related U.S. Application Data

(60) Provisional application No. 61/952,553, filed on Mar. 13, 2014.

(51) Int. Cl.
*A61M 16/12* (2006.01)
*A61B 5/055* (2006.01)
(Continued)

(52) U.S. Cl.
CPC ........... *A61M 16/122* (2014.02); *A61B 5/087* (2013.01); *A61M 16/0051* (2013.01); *A61M 16/026* (2017.08); *A61B 5/055* (2013.01); *A61B 5/742* (2013.01); *A61M 16/085* (2014.02); *A61M 16/0808* (2013.01); *A61M 16/0875* (2013.01); *A61M 16/16* (2013.01); *A61M 2016/0027* (2013.01); *A61M 2016/0039* (2013.01); *A61M 2016/1035* (2013.01); *A61M 2202/0208* (2013.01); *A61M 2202/0275* (2013.01); *A61M 2205/05* (2013.01); *A61M 2205/18* (2013.01); *A61M 2205/50* (2013.01); *A61M 2205/502* (2013.01)

(58) Field of Classification Search
CPC ............ A61B 5/055; A61M 2016/003; A61M 2202/0275; A61M 16/00; A61M 16/0003; A61M 16/0057; A61M 16/0051; A61M 16/06; A61M 16/0666; A61M 16/085; A61M 16/0875; A61M 16/12; A61M 16/122; A61M 16/16; A61M 2205/05; A61M 2205/18; A61M 2205/50
USPC .......................................................... 424/718
See application file for complete search history.

(56) References Cited

U.S. PATENT DOCUMENTS 4,614,208 A * 9/1986 Skarelius ................. F16L 9/12
  138/103
5,558,083 A   9/1996 Bathe et al.
(Continued)

OTHER PUBLICATIONS

"FDA Clears Nitric Oxide Inhalation Device for MRI Procedues"; retrieved from https://www.meddeviceonline.com/doc/fda-clears-no-gas-delivery-device-to-be-used-during-mri-procedues-0001.*
(Continued)

*Primary Examiner* — (Jackie) Tan-Uyen T Ho
*Assistant Examiner* — Joseph D Boecker (57) ABSTRACT

The present invention relates to a device and method of delivering inhaled Nitric Oxide (iNO) to a patient situated in a Magnetic Resonance Imaging (MRI) suite.

18 Claims, 2 Drawing Sheets

(51) Int. Cl.
*A61M 16/00* (2006.01)
*A61M 16/06* (2006.01)
*A61M 16/08* (2006.01)
*A61M 16/16* (2006.01)
*A61B 5/087* (2006.01)
*A61M 16/10* (2006.01)
*A61B 5/00* (2006.01)

(56) References Cited

U.S. PATENT DOCUMENTS

| | | | |
|---|---|---|---|
| 5,732,693 | A | 3/1998 | Bathe et al. |
| 5,752,504 | A | 5/1998 | Bathe |
| 6,125,846 | A | 10/2000 | Bathe et al. |
| 6,253,764 | B1* | 7/2001 | Calluaud ............... A61M 16/20 128/204.18 |
| 7,523,752 | B2 | 4/2009 | Montgomery et al. |
| 8,282,966 | B2 | 10/2012 | Baldassarre et al. |
| 8,291,904 | B2 | 10/2012 | Bathe et al. |
| 8,293,284 | B2 | 10/2012 | Baldassarre et al. |
| 8,431,163 | B2 | 4/2013 | Baldassarre et al. |
| 8,573,209 | B2 | 11/2013 | Bathe et al. |
| 8,573,210 | B2 | 11/2013 | Bathe et al. |
| 8,770,199 | B2 | 7/2014 | Flanagan et al. |
| 8,776,794 | B2 | 7/2014 | Bathe et al. |
| 8,776,795 | B2 | 7/2014 | Bathe et al. |
| 8,795,741 | B2 | 8/2014 | Baldassarre |
| 8,846,112 | B2 | 9/2014 | Baldassarre |
| 2007/0149891 | A1* | 6/2007 | George ............... A61B 5/0813 600/533 |
| 2008/0251082 | A1* | 10/2008 | Sinha ............... A61M 16/0045 128/207.16 |
| 2010/0331667 | A1* | 12/2010 | Nelson ............... A61B 5/02141 600/411 |
| 2011/0253136 | A1* | 10/2011 | Sweeney ............... A61M 16/16 128/203.12 |
| 2012/0240927 | A1* | 9/2012 | Bathe ............... A61M 16/20 128/203.12 |
| 2014/0190481 | A1* | 7/2014 | Jam ............... A61M 16/0006 128/203.12 |
| 2015/0168519 | A1* | 6/2015 | Rapoport ............... A61B 5/055 324/318 |
| 2015/0265787 | A1* | 9/2015 | O'Connor ......... A61M 16/0051 128/204.23 |
| 2016/0158481 | A1* | 6/2016 | Klein ............... A61M 16/12 128/203.14 |

OTHER PUBLICATIONS

Devendra, Ganesh P., et al., Modified INOvent for delivery of inhaled nitric oxide during cardiac MRI, *Magnetic Resonance Imaging* 2011, 5 pages.

Radford, Edward P., et al., Clinical Use of Nomogram to Estimate Proper Ventilation During Artificial Respiration, *N. Engl. J. Med.* vol. 251 No. 22 1954, 877-884.

INOmax DS (Delivery System): Operation Manual (800 ppm INOMAX (nitric oxide) for Inhalation), *Ikaria, Inc.* 2010, 112 pages.

INOvent Delivery System: Operation and Maintenance Manual (CGA Variant), *Datex-Ohmeda, Inc.* 2000, 180 pages.

Using the INOpulse DS Subject Guide, *Ikaria, Inc.* 2012, 50 pages.

INOmax Label, Nitric Oxide Gas, *INO Therapeutics* 2013, 2 pages.

INOmax DSIR (Delivery System): Operation Manual (800 ppm INOMAX (nitric oxide) for Inhalation), Ikaria, Inc. 2012, 136 pages.

* cited by examiner

GAS DELIVERY DEVICE AND SYSTEM FOR USE IN MAGNETIC RESONANCE IMAGING

CROSS-REFERENCE TO RELATED APPLICATIONS

This application claims, under 35 USC § 119(e), the benefit of U.S. Provisional Application No. 61/952,553, filed Mar. 13, 2014, the contents of which is hereby incorporated by reference in its entirety.

TECHNICAL FIELD

Embodiments of the present invention generally relate to the field of devices and methods for nitric oxide delivery to a patient situated in a Magnetic Resonance Imaging (MRI) suite.

BACKGROUND OF THE INVENTION

Inhaled nitric oxide (iNO) is used as a therapeutic gas to produce vasodilatory effect on patients. When inhaled, NO acts to dilate blood vessels in the lungs, improving oxygenation of the blood and reducing pulmonary hypertension. Because of this, nitric oxide is provided in inspiratory breathing gases for patients with various pulmonary pathologies including hypoxic respiratory failure (HRF) and persistent pulmonary hypertension (PPH). The actual administration of iNO is generally carried out by its introduction into the patient as a gas along with other normal inhalation gases. Such administration must be added in synchrony with the respiration pattern of the patient.

Magnetic resonance imaging (MRI) is a medical imaging technique used to visualize internal structures of a patient's body in detail. The MRI device utilizes large, powerful magnets in its operation. The very high strength of the magnetic field created by an MRI device can cause "missile-effect" accidents, where ferromagnetic objects are strongly attracted to the magnet resulting in danger to the patient and clinicians. To reduce the risks of projectile accidents, ferromagnetic objects and devices are typically prohibited in proximity to the MRI device and patients undergoing MRI examinations are required to remove all metallic objects. The safety of the patient and/or MRI device can be compromised by magnetically induced displacement forces and torque, Radio Frequency (RF) and gradient-induced heating/voltages/vibration, unintentional output and operational inhibition (device malfunction), etc. MRI compatibility issues, such as materials causing MR image artifacts or decreases in the MR image quality, can lead to diagnostic errors (inaccuracies/misinterpretations), significant lack of information and difficulties with follow-up exams.

During the management of HRF and PPH in neonates and adults it is often necessary to conduct imaging studies wherein iNO treatment is used in conjunction with head cooling procedures, measurement of cardiac shunting, and the measurement of pulmonary blood flow. While computed tomography (CT) scans are currently the mainstay for these procedures, concerns about exposure to CT-based radiation has been increasing, particularly for neonates. As a result, many clinicians would prefer to use MRI for conducting imaging in neonates. However, current nitric oxide delivery devices are not compatible for use in the high magnetic environment of a magnetic resonance imaging machine and therefore, it is currently not possible to deliver nitric oxide to a patient situated in an MRI suite. Moreover, abrupt or premature discontinuation of iNO treatment can result in rebound hypertension, which may result in adverse events as serious as death.

Therefore, there is a need for a device and method to allow for the safe administration, monitoring and display of the NO concentration to a patient situated in a MRI suite.

SUMMARY OF THE INVENTION

One aspect of the present invention pertains to a nitric oxide delivery system for providing inhaled nitric oxide to a patient situated in an MRI suite comprising a patient connector; a source of nitric oxide gas; a source of breathing gas; a monitoring control circuit; a delivery control circuit; a signal processor; a humidifier and an injector module fluidly connected to the supply of nitric oxide, the supply of breathing gas and the delivery control circuit; the injector module being located beyond an iso-gauss safety line.

In one or more embodiments, the patient connector may be a wye or a nasal cannula. In one or more embodiments, the patient connector comprises an inspiratory limb and an expiratory limb.

In one or more embodiments, the monitoring control circuit may comprise a monitor CPU, a zero valve, sample pump, sampling port, sample flow sensor, and gas sampling bench. In one or more embodiments, the delivery control circuit may comprise a pressure transducer, a backup on/off switch, a pressure regulator, shutoff valve, a proportional control valve, and a flow sensor. The flow sensor may be a thermal mass flowmeter, pneumotach, hot wire anemometer, thermal flow sensor, variable orifice, thermal time-of-flight, or rotating vane.

In one or more embodiments, the signal processor may be a central processing unit (CPU) including a corrective signal processing algorithm. The corrective signal processing algorithm removes distortion and delay caused by an increased length of delivery tube. In one or more embodiments, the corrective signal processing algorithm comprises a determination of an inverse of a distortion transfer function produced by a long iNO delivery tube; a determination of a ventilator flow profile of individual breaths performed on a continuing basis during ventilation; a convolution of the inverse of a distortion transfer function with a predicted breath flow profile; and verification of a consistent ventilator flow profile.

In one or more embodiments, the source of nitric oxide gas may be of a known concentration. In one or more embodiments, the source of breathing gas may be a mechanical ventilator.

In one or more embodiments, the nitric oxide delivery system further includes an alarm system operable by a signal from the signal processor indicative of a pre-determined concentration of NO.

In one or more embodiments, the injector module may be located downstream from the humidifier.

Another aspect of the present invention pertains to a nitric oxide delivery system for providing inhaled nitric oxide to a patient situated in an MRI suite comprising a patient connector; a source of nitric oxide gas; a source of breathing gas; a monitoring control circuit; a delivery control circuit; a signal processor; a humidifier; and an injector module fluidly connected to the supply of nitric oxide, the supply of breathing gas and the delivery control circuit. In one or more embodiments, the injector module may be located inside an iso-gauss safety line and/or upstream from the humidifier.

In one or more embodiments, the injector module or the entire device is made of non-ferrous materials.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

MRI suites present unique dangers for patients and staff due to the high-strength magnetic field utilized in clinical MRI devices. In response to this risk, MRI equipment manufacturers and government regulators recognize the "gauss exclusion zone" which defines a three-dimensional bubble of magnetic force to which access is to be limited to only those persons and items that have successfully cleared screening for prohibited ferrous-containing, metallic and other magnetic objects and devices.

Also, an MRI suite presents risk of damage to other medical devices that may be located in the MRI suit due to the magnetic force/torque and RF energy.

The present invention provides a device and method for a safe delivery of inhaled nitric oxide (iNO) to patients undergoing an MRI examination. Such patients must stay or be made to be immobile for brief periods of time. Such patients may generally fall into the following two classifications: 1) patients who are pharmacologically comatose and 2) patients who have enough control of their faculties to remain unmoving based on command. The former patients may consist of small children or babies. Such small children or babies would be mechanically ventilated using machine delivered breaths which are repeating and predictable. The latter group would consist primarily of larger children and adults who, as a group, would have predictably lower respiratory rates and would be less affected by a timewise delay due to the relative slower breath rate or a distortion in measured iNO concentration.

Figure 1:
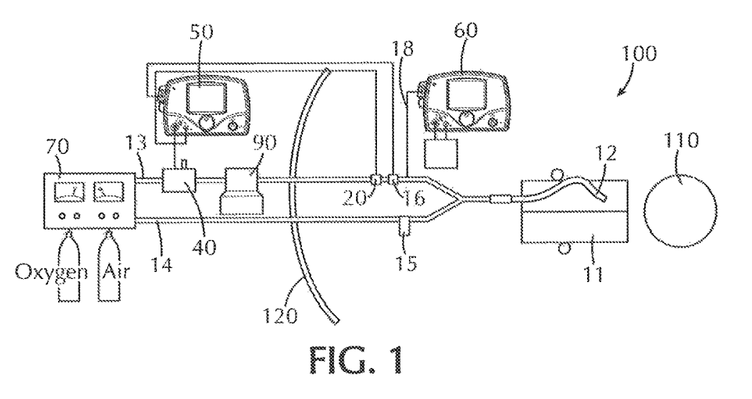
FIG. 1 is a schematic view of a nitric oxide delivery system including a nitric oxide delivery device, a ventilator, a gas source, a control module and injection module according to one or more embodiments wherein the placement of injector module is outside an iso-gauss line with the nitric oxide injector module port capped and both the NO injection tube and sampling Tees being positioned just proximal to the patient WYE.

One aspect of the present invention pertains to a gas delivery device to be utilized in an MRI suite that includes an injector module situated outside of the gauss exclusion zone wherein said injector module is connected to a valve assembly in communication with a control module to control the delivery of gas from a gas source and ventilator to introduce the gas into the patient via a wye, nasal cannula, endotracheal tube, face mask or the like. Placement of an injector module outside of the gauss exclusion zone of an MRI suite or in low magnetic field, and thus away from the strong magnetic field of the MRI, allows the nitric oxide delivery system to deliver nitric oxide at constant inspiratory concentration without the potential confounding effects of flow measurement distortion which might be present when the injector module is placed in close proximity to the magnetic field. The significant absence of such flow measurement distortion ensures that the patient receives a highly constant and controllable concentration of nitric oxide in the inspiratory gas stream. As shown in FIG. 1, the MRI suite 100 includes a MRI machine 110 and ISO-Gauss Safety line 120. A health care provider selects the desired concentration of NO that is to be administered to the patient 11 by means of an input to the delivery CPU via a keyboard, dial, encoder, touch screen, thumb wheel or the like.

The patient 11 in need of an MRI examination is placed within the MRI machine 110 located within the ISO-Gauss Safety line 120. The patient 11 is connected to a ventilator 70 and nitric oxide delivery device 10 via a wye 12.

As shown in FIG. 1, wye 12 includes an inspiratory line 13 and an expiratory line 14 of conventional design. The inspiratory limb 13 carries gas to the patient and the expiratory limb 14 carries gas exhaled by the patient to the ventilator 70. The inspiratory limb 13 of the ventilator 70 may include a sample tee 16 for facilitating fluid communication between the inspiratory limb 13 of the breathing circuit and the sample line 18. Expiratory line 14 includes a water trap 15 downstream from the patient 11. The expiratory line 14 connects to the ventilator 70 further downstream from the water trap 15.

Inspiratory line 13 of wye 12 includes a sample tee 16 upstream from the patient, which connects to monitoring control circuit 60. Since the sampling tee 16 and gas injection tee 20 are placed just proximal to the patient wye 12, lower levels of nitrogen dioxide ($NO_2$) are formed while delivering NO within a desired range. It should be noted that $NO_2$ formation is the result of both nitric oxide and oxygen mixing as well as the residence time (or time duration of mixing) and, thus, minimization of residence time minimizes the amount of $NO_2$ formation. As shown in FIG. 1, the placement of injector module 40 beyond the iso-gauss line with the injector port capped and both the NO injector and sampling tees of the gas mix being positioned just proximal to the patient WYE allows for minimal contact duration between inspiratory oxygen and injected NO. In one or more embodiments, ventilator inspiratory flow is measured near the ventilator. An increase in length of the injector module tube (which injects nitric oxide into the breathing circuit) could lead to additional gas transport delays and therefore significant ventilator/waveform disynchrony. Such disynchrony could potentially lead to significant amounts of NO being delivered to the circuit well behind the ventilator flow pattern and therefore leading to errors in delivered NO. A corrective algorithm may be included to correct or minimize the waveform disynchrony at the nitric oxide delivery device.

Monitoring control circuit 60 includes a monitor CPU connected to a zero valve, sample pump, sample flow sensor, gas sampling bench as discussed below in detail.

The sample flow sensor monitors the flow of breathing gas from the breathing gas delivery system. One or more indicators or alarms may be present to inform a user of the device when the flow of breathing gas rises above or falls below a predetermined level. The sample flow sensor senses the flow of gas from the gas delivery system and uses that information with a selective algorithm to provide a desired concentration of NO to the patient. As used herein, the term gas delivery system is intended to include various types of gas proportioning devices, gas mixers and various types of mechanical ventilators used to provide breathing gas to a patient.

A sampling port is included in the monitor control circuit 60 which communicates with the flow of gas passing through the inspiratory limb. The sampling port samples the mixed gases as sampled distal to the injector module 40 where the NO/nitrogen stream of gas is mixed with the inspiratory gas from the gas delivery system.

Accordingly, the flow from the gas delivery system 50 enters the inlet at a flow rate $Q_i$ and at a certain concentration of oxygen and is mixed in the injector module 40 with the NO/nitrogen gas from proportional control valve. In one or more embodiments, the injector module 40 is placed outside of the Iso-Gauss line with the gas injection inlet of the injector module 40 capped. The injector module 40 shown in FIG. 1 is in fluid communication with the nitric oxide gas source via the injector tubing and in electronic communication with the delivery control module 60 via the injector module cable such that the delivery control module 60 can detect and regulate the flow of gas from the gas source to the ventilator 70. Specifically, the injector module 40 is in fluid communication with the gas source 70 via an injector tubing, which is in fluid communication with one or more of the pressure switch, pressure shut-off valve, proportional valve, flow sensor and the backup switch of the delivery control module 50. The injector module 40 may also be in electronic communication with the delivery control module 50 via an injector module cable. Flow sensor is upstream of the injector module 40 and thus senses the flow only of the gas from the gas delivery system while sampling port 80 is downstream of the injector module and thus provides access to samples of the gases that are mixed together at injector module 40. At injector module 40, there may be a diffuser that enhances the mixing of the NO/nitrogen with the gases from the gas delivery system.

Therefore, the concentration of mixed gases at sampling port 80 contains the concentration of NO that actually enters the patient for therapeutic treatment and is the concentration set on the machine by the health care provider.

The monitor CPU may also be in communication with a sample flow sensor for sensing the flow of the sample drawn via sample line, a pump for drawing the sample via the sample line to the flow sensor and check/zero valve controlling the flow of the sample via the sample line to the sample pump, sample flow sensor and the plurality of CPU sensors. The sample line may include a water trap 15 for collecting any water or liquid from the sample.

Connected to the sample flow sensor is a gas sensing bench and which analyzes the concentrations of certain components ($O_2$, NO and $NO_2$) of the gas stream administered to the patient. In the preferred embodiment, the gas sensing bench samples the gases through conduit and senses and quantifies the concentration of NO, as well as, $NO_2$ and $O_2$. The gas sensing bench provides for continuous monitoring of the actual NO concentration administered to the patient and therefore is a further safety monitor. In the event the NO detected by the gas sensing bench is a predetermined value away from the set point established by the user, an alarm may be triggered so the user can attend to the problem. In the event that the $NO_2$ level rises to a dangerous level, delivery CPU can discontinue use of the NO to the patient by shutting off the shutoff valve or by automatically reducing the NO level to a lower, safe level established in the system.

A signal processing means, such as a CPU is provided to solve certain equations and algorithms to operate the nitric oxide delivery system. CPU may be configured to receive a signal from an input device indicative of the concentration the user desires to be administered to the patient. CPU also may be configured to receive signals from the flow transducer indicative of the flow of gas delivered by the gas delivery system through a signal line and also receives signals indicative of the concentration of NO, as well as $NO_2$ and $O_2$ from gas sensor bench via a signal line, and a signal from a flow sensor indicative of the flow from proportional control valve, via a signal line. The central processing unit may be one of many forms of a computer microprocessor/microcontroller that can be used in an industrial or medical setting for controlling various medical gas flow devices and sub-processors. The CPU can be coupled to a memory (not shown) and may be one or more of readily available memory such as random access memory (RAM), read only memory (ROM), flash memory, compact disc, floppy disk, hard disk, or any other form of local or remote digital storage. Support circuits (not shown) can be coupled to the CPU to support the CPU in a conventional manner. These circuits include cache, power supplies, clock circuits, input/output circuitry, subsystems, and the like.

Another input to monitor CPU is provided by the NO sensor through signal line. The NO sensor senses the concentration of NO in the supply cylinder so that the user can verify that the proper supply is being utilized or, alternatively, the CPU may use that input to adjust the system to adapt for any concentrations of NO in the supply within certain limits. NO sensor could, of course, be eliminated if the NO cylinder is always constant or by keying into the NO sensor in the gas sensing bench.

Further downstream from the sample tee 16 beyond ISO-Gauss Safety line 120, inspiratory line 13 connects to humidifier 90. Further downstream from humidifier 90, inspiratory line 13 connects to injector module 40. Alternatively, the injector module 40 may be provided upstream of the humidifier. Injector module 40 connects to delivery control circuit 80. Delivery control circuit 80 includes a delivery CPU connected to a flow sensor, proportional valve, shut off valve, and pressure regulator as discussed below in detail. Further downstream from injector module 40, inspiratory line 13 connects to ventilator 70.

In accordance with the present invention, there is provided a nitric oxide delivery system in an MRI suite that is useable with various means of administering a breathing gas, including the use of any mechanically assisted ventilation and ventilatory pattern, such as a ventilator. A forced ventilation device, such as a mechanical ventilator, may be used where a varying flow of breathing gas is delivered to the patient as well as gas blenders or proportioners that supply a continuous flow of the breathing gas to the patient to which NO has been added. The precise flow from the ventilator must be known and then the amount of NO to be added is determined on a case-to-case and moment-to-moment basis.

A supply of nitric oxide may be provided in the form of a cylinder of iNO gas connected to the shut off valve beyond ISO-Gauss Safety line 120. The iNO gas is preferably nitric oxide mixed with nitrogen or some other gas, preferably an inert gas, and is a commercially available mixture. A cylinder of nitric oxide is delivered pressurized and a typical pressure is on the order of about 3000 psi with a concentration of nitric oxide in the order of about 800 ppm. In one or more embodiments, an additional supply of nitrogen or some other gas, preferably an inert gas, may be provided to dilute, if necessary, the concentration of nitric oxide in the supply to the shutoff valve to a desired amount. For example, the cylinder may be supplying a concentration of nitric oxide that is too high for the particular flows in the system and therefore the concentration may be reduced to a more desirable level. Alternatively, the NO/nitrogen gas may be available in a central supply within a hospital and be available through the normal hospital piping system to various locations such as MRI suite or operating rooms.

The delivery module 50 may include a pressure switch for determining a gas supply pressure is present. The delivery module 50 may also include a backup on/off switch. The delivery control circuit 80 includes a pressure regulator to reduce the pressure of the gas in cylinder down to acceptable levels for operation of the gas delivery system. Shutoff valve receives the reduced pressure gas from regulator through a suitable conduit and is preferably solenoid operated.

The delivery control circuit 80 also includes a proportional control valve that provides a predetermined flow of nitrogen through a suitable conduit into the injector module.

The delivery control circuit 80 also includes a flow sensor located downstream from proportional control valve which senses the flow from the proportional control valve. In one or more embodiments, the flow sensor may be a thermal mass flowmeter, pneumotach, hot wire anemometer, thermal flow sensor, variable orifice, thermal time-of-flight, rotating vane and the like. A flow sensor may also be used that actually measures pressure, such as a pressure drop though an orifice, in order to determine flow.

In one or more embodiments of this aspect, the monitor control circuit 60 includes a monitor CPU in communication with a flow controller, wherein the monitor CPU sends and receives signals to the flow sensor and the flow controller such that the control circuit maintains a minimum flow of therapeutic gas to the patient. In the preferred embodiment, the monitor CPU obtains information from the flow sensor and from an input device that allows the user to select the desired concentration of NO to be delivered to the patient and calculates the flow of NO/nitrogen to obtain that selected concentration. By use of the monitor CPU, various algorithms may be stored and used as appropriate. For example, there may be one algorithm that is used to obtain a steady concentration of NO in a spontaneous or continuous flow situation such as when a gas proportioner of gas blender is used. A differing use of that same algorithm may be used to achieve a rapid change in the NO/nitrogen supply flow to maintain the desired flow to the patient or, that same algorithm may be used to calculate a breath-by-breath flow of NO/nitrogen such that the flow from the gas delivery system may be determined and used to adjust the NO/nitrogen flow to maintain the desired NO concentration to the patient in the next breath delivered to the patient. In any manner, the delivery CPU takes over the manual setting of any valves and established the concentration of NO to the patient as set or selected by the user.

The delivery CPU receives input regarding the flow of breathing gas from the gas delivery device by means of flow sensor and the concentration of NO in the NO/nitrogen supply by means of NO sensor. With that information, delivery CPU can calculate the desired flow from the proportional control valve that needs to be provided to the injector module 40 to mix with the gas from the gas delivery system to produce the desired or set concentration established by the user through input device. The delivery CPU uses an equation or algorithm to calculate the flow of NO/nitrogen to be added to the injector module 40. Thus, the concentration of NO to the patient can be changed at a rapid rate limited only by the speed and sensitivity of the components such as flow transducer. The faster the response of flow transducer is, the faster changes can be made in flow of the NO/nitrogen to injector module 40 by proportional control valve such that the NO to the patient can account for changes in the flow profile from the gas delivery system to maintain that concentration set by the user. The flow delivered from the proportional control valve to the injector module 40 is determined from the concentration set by the user. The delivery CPU can make changes to the flow delivered from proportional control valve in order to maintain the concentration of the combined flows delivered to the patient at the desired level as determined by the user. Control signals are transmitted from delivery CPU to proportional control valve, shutoff valve, and pressure regulator via signal lines.

As an alternate, the system may operate on a breath-by-breath basis such that the system can take a reading of the flow, or a portion thereof, from the gas delivery system at each breath and calculate the desired flow of NO/nitrogen for delivery at the next breath. With the breath-by-breath analysis, however, the flow sensor may detect the start and end of a breath, or selected portion thereof, integrate to determine the total or fixed selected volume of the breath, and adjust the proportional control valve to provide the set or desired concentration of NO at the next breath.

For constant or continuous flow ventilation from the gas delivery system, since the flow is continuous and the tidal volume assure to be constant, the flow from the gas delivery system may be sampled at a relatively slow rate, for example, once per second, and the flow of NO/nitrogen calculated and established from proportional control valve on that particular timing cycle.

By knowing the flow from the gas delivery system by means of flow sensor and the concentration of NO from NO sensor, a derivation is made by the delivery CPU and the proportional control valve is adjusted to provide then calculated flow of NO/nitrogen to arrive at the desired concentration set by the user in the breathing gas actually administered to the patient.

Confirmation of the flow from the proportional control valve is made by the flow sensor so that monitoring CPU can check to see of the actual flow corresponds to the flow calculated and established by the CPU through signal line to proportional control valve. Alternatively, the flow sensor can control the proportional control valve using a feedback system.

CPU also controls the proportional control valve via signal line and can operate that valve to further reduce the concentration of the NO in nitrogen from cylinder in the event very low concentrations are set by the user and the system is otherwise unable to reduce the concentration to the desired point.

It will be noted, however, that while a CPU is preferred, the signal processing needed by this system can readily be accomplished through the use of alternate technologies, such as analog or digital circuitry, fluidic circuits, optical means or mechanical components. The term "signal processing means" is intended to encompass the variety of ways that may be utilized to carry out the various signal processing functions to operate the subject NO delivery system.

In one or more embodiments, a button may be placed on the display console of the control circuit to switch the sampling software to "MRI mode" to utilize the corrective algorithm. A lengthened supply and sampling tubes may be used for MRI Suites wherein the tubing would be available in a few known lengths to make the signal processing easier to implement mathematically and the length of the tube used would be dialed or entered in by the healthcare provider.

Tubing ID changes in the NO supply tubing may be implemented (in the case of smaller tubing IDs) to reduce the temporal distortion effects imposed by gas transport delay within the tubing. However, such changes in tubing ID must be compatible with the existing flow delivery pneumatics for which increases in tubing restriction and/or resistance accompanying such ID reductions can produce adverse effects on, for instance, the sampling pump and sampling flow delivery pneumatics. Further, any length of NO delivery tubing is subject to $NO_2$ formation within the delivery tube due to oxygen diffusion/ingress across the walls of the tubing and into the space in which the NO/Nitrogen mix is housed and delivered. Longer lengths of tubing may be problematic in this respect as the greater amount of overall tubing surface area provides more opportunity for oxygen ingress. A further aspect of this invention includes the use of tubing materials and or coatings which minimize oxygen ingress thereby limiting $NO_2$ formation. Such tubing is described in detail in U.S. Pat. No. 8,770,199, issued to Flanagan et al. on Jul. 8, 2014, which is incorporated herein by reference in its entirety for all purposes. Such low oxygen permeation NO supply tubing may be used in isolation, or in combination with longer tubing lengths with smaller IDs to minimize both temporal flow distortion effects and $NO_2$ buildup effects in the NO delivery tube.

Special MRI Mode Signal Processing:

iNO concentration delay/distortion may result due to the lengthened flow delivery tube. In addition, movement of an injector module into the magnetic field of the MRI may result in iNO signal distortion. The injector module may also produce distorted output signals due to the analog circuitry on the module's circuit board when placed in close proximity to the strong magnetic field. Thus, the concomitant use of an injector module placed outside the MRI suite and a distortion/delay removing signal processing algorithm enacted by the health care provider by enabling an MRI mode on the nitric oxide delivery device must be employed to produce non-distorted/delayed iNO delivery to the patient to ensure that the fidelity of the iNO concentration profile is maintained. Signal processing schemes may include a special MRI mode which can be entered into the nitric oxide delivery device by the health care provider. This special MRI mode would engage the signal processing algorithms.

An exemplary predictive algorithm for propagation delay/distortion removal will now be discussed which represents one way to perform the removal of the distortion caused by the long delivery tube. A corrective signal processing algorithm removes and/or compensates for the ventilator/waveform disynchrony introduced by the gas transport delays within a length of a delivery tube connected to the gas injection tee. Those skilled in the art might come up with similar signal processing schemes; however, any such schemes which solve the problem addressed here should be viewed as within the scope of this invention. A so-called "predictive" algorithm can be implemented which would effectively remove the delay and distortion artifact from the long iNO gas flow tubing path. This long path would serve to both delay and distort the original iNO concentration signal. Such an algorithm would be implemented on the (input or commanded) iNO signal from the device. This algorithm would be implemented on predicted waveforms and used to modify commanded iNO concentration from the nitric oxide delivery device. The algorithm would consist of four primary components as follows: 1) determination of an inverse of the distortion transfer function produced by the long iNO delivery tube; 2) determination of the ventilator flow profile of individual breaths should be performed on a continuing basis during ventilation; 3) convolving the inverse of the distortion transfer function with the next "predicted" breath flow profile and delivering this flow profile from the nitric oxide delivery device should be performed for each breath period; and 4) verifying that the ventilator flow profile has not changed, thereby allowing step 3 to be repeated on the next ventilator breath and to be performed for each breath period.

Determination of an Inverse of the Distortion Transfer Function of the Long iNO Delivery Tube Signal distortion due to the long tube can be readily characterized in the frequency domain if both the input and output signal are known. The (known) input signal is (in the time domain) convolved by the (long tube generated) distortion transfer function (or multiplied in the frequency domain) to obtain the measured output. In order to reverse the effects of the distortion in the iNO concentration signal due to the long tube, the known input signal can be convolved (in the time domain) or multiplied (in the frequency domain) with a special "inverse filter" which is in fact, the inverse of the distortion transfer function. The result of convolving the input signal with the inverse filter would be an output signal which proactively corrects for the anticipated distortion created by the long tubing.

First the distortion transfer function must be determined and must be time invariant such that the tubing length must never change, or must be fixed. Further, the transfer function of the distortion must be determined using varying (coupled) input and output concentration values. Such a determination of system transfer functions based on the relationship of input to output is well known in the art.

Once the distortion transfer function is known, it must be inversed to obtain the inverse filter (transfer function). Inverse filtering can be a difficult proposition if significant noise is added to the output signal, therefore another type of algorithm which can be used in lieu of typical inverse filtering techniques is Wiener deconvolution. This strategy can counter the confounding effects of noise on the output signal leading to a better estimation of the inverse of the distortion transfer function.

Once the inverse filter is defined mathematically, it can be convolved with the input iNO flow signal to obtain the iNO flow signal to be commanded by the machine which will result in non-distorted output. This non-distorted output (in this case non-distorted iNO concentration over time) will be the result (as delivered to the patient).

Determination of the Ventilator Flow Profile

Determination of the flow profile of individual breaths must be performed on a continuing basis during ventilation. In order to implement the type of predictive algorithm of the present invention, the signal (in this case the ventilator flow signal) must be determined ahead of time, and therefore must be a repeating signal ideally with minimal noise artifact. Such signals exist when babies and small sedated children are being ventilated using machine delivered breaths. For such patients, repeating breath patterns are set on the ventilator. The need therefore exists for the algorithm to determine what each segment of this repeating flow profile looks like. There are any number of ways to do this of which two will be described here. First, a fixed length of signal can be captured and compared to similar previous fixed length segments using autocorrelation (minimization). Appropriate lengths of the segments need to be determined. A second method would be by using a repeating signal characteristic in the breath such as a rapidly declining inspiratory flow to signal a stop or start point for the segment.

Convolving the Inverse of the Distortion Transfer Function with the Next "Predicted" Breath Flow Profile Convolving the inverse of the distortion transfer function with the next "predicted" breath flow profile must be performed for each breath period. Therefore, once the ventilator flow segment that repeats is identified, it must be convolved with the inverse of the distortion transfer function (i.e. inverse filter). This would be performed mathematically by the embedded processor of the nitric oxide delivery device for one breath segment. This newly derived flow sequence would then be fed to the flow delivery device of the nitric oxide delivery device.

Verification of Ventilator Flow Profile

The flow profile must be verified for each breath period to ensure that the flow profile has not changed. Finally, the mean value of a predetermined number of last breath segments must be determined. This is done by simply taking the current breath segment and adding it to a buffer containing the last (X−1) breaths which can be averaged over the number of breaths in the buffer. The result would be an averaged representation of the last X breath segments. Once this is complete, each time a new breath is in the process of being delivered, this breath can be compared to the mean of the previous X breaths, if significant disparity exists between the current breath and the mean of the previous X breaths, then the algorithm must be abandoned in favor of the nitric oxide delivery device's existing flow algorithm until such time as the above difference is within a pre-selected defined bounds.

In one or embodiments, an $NO_2$ correction algorithm may be included in which the measured $FiO_2$, the measured NO concentration and potentially other critical variables are used to estimate the over-measurement of $NO_2$ for later correction in the display.

The concentration of iNO administered to a patient situated in an MRI suite will vary according to the patient and the need for the therapy. The concentration must be precisely metered to the patient since an excess of NO can be harmful to the patient. In addition, the administration must be efficient in a timely manner in that NO is oxidized in the presence of oxygen to nitrogen dioxide and which is a toxic compound.

The device may also include various controls, alarms and safety devices to prevent excess concentrations of $NO_2$ in the administration of NO to the patient, including means to shut down the NO system or to reduce the NO concentration to the patient to a safer level. The NO delivery system may thus provide an alarm or other appropriate action in the event of an increase in the NO level beyond a predetermined level, a decrease in $O_2$ below a predetermined level and/or an increase of $NO_2$ above a predetermined level. In certain embodiments, the indicator/alarm provides an alert when the flow of breathing gas rises above or falls below a predetermined level. As an alternate embodiment, a further means is included that adjusts the $O_2$ concentration to the patient to compensate for the diminution of $O_2$ to the patient as the patient inspiratory gas is loaded with NO/nitrogen to achieve a specified concentration of NO in the patients inspired gases.

According to one or more embodiments, the alert includes one or more of an audible alert, a visual alert and/or a text alert.

One or more embodiments of this aspect provide that the device further comprises a display that provides a visual and/or numeric indication of the volumetric flow of breathing gas. In certain embodiments, the visual and/or numeric indication includes one or more of volumetric flow rate, tidal volume, and/or minute ventilation.

Another aspect of the invention relates to a method of monitoring the delivery of therapeutic gas to a patient comprising providing a flow of breathing gas, providing a flow of therapeutic gas comprising nitric oxide, delivering the breathing gas and therapeutic gas to a patient situated in an MRI suite, measuring the flow of breathing gas to obtain a measured flow of breathing gas, and displaying the measured flow of breathing gas on a display module. In one or more embodiments, displaying the measured flow of breathing gas includes displaying one or more of volumetric flow rate, tidal volume, and/or minute ventilation.

According to one or more embodiments, the method further comprises comparing the measured flow of breathing gas to a predetermined flow limit and providing an alert if the measured flow of breathing gas is above or below the flow limit. In certain embodiments, the alert includes one or more of an audible alert, a visual alert and/or a text alert. In certain embodiments, the method further comprises adjusting the flow of breathing gas delivered to the patient in response to the alert.

A purge valve may be included to purge the system of any other gases that may be in the supply line and refill the supply lines from cylinder to the purge valve with fresh NO/nitrogen so that the system is recharged with the correct supply gas and no extraneous gases, such as ambient air. A ventilator 70 may be used to provide an oxygen supply to the patient.

In one or more embodiments, the delivery control CPU may be configured to communicate with the monitor CPU via a transceiver that transmits a wireless optical line-of-sight signal during a pre-determined interval signal from the monitoring CPU to the delivery control CPU transceiver. Communication between the delivery control CPU and the monitor control CPU may also be established via a cable.

The ventilator 70 shown in FIG. 1 is in fluid communication with the control module via an injector tube and in electrical communication via an injector module cable. Tubing lengths including patient circuits, the sampling tube, and the injector tube may be extended to represent the anticipated distance between the MRI imager and the iso-gauss line beyond which the nitric oxide delivery device is expected to be located during imaging. The control module and more specifically, the CPU, is in fluid communication with the ventilator 70 via the sample line. The ventilator may include a breathing circuit with an inspiratory limb 13 and an expiratory limb 14 in fluid communication with the ventilator 70. The inspiratory limb 13 may be in fluid communication with a humidifier, which is in fluid communication with the ventilator via an injector module 40.

In one or more embodiments, the control module includes a display for providing visual indication to the user the components of the gas being delivered from the gas source to the ventilator 70 (e.g., NO, $O_2$, $NO_2$), the concentration of each component and whether communication has been established with one or more gas sources. Visual alarms may also be displayed on the display. The control module may also include a control wheel allowing the user to navigate through various displays or information displayed on the display. An injection module tubing outlet may be disposed on the control module for providing fluid communication between the delivery module and the injector module. An injection module cable port may also be provided on the control module to provide electronic communication between the delivery module and the injector module. The control module also includes the sample line inlet in fluid communication with the sample line and the inspiratory limb of the ventilator. In one or more embodiments, a water trap may be disposed on the control module, adjacent to the sample line inlet.

The control module also includes a plurality of inlets on the back of the control module. In one or more embodiments, two gas inlets, for connecting the control module to the gas source are provided and one auxiliary inlet for connecting the control module to an auxiliary gas source, which may include oxygen or other gas. A power port is also provided on the back of the control module to connect the control module to an AC/DC power source.

The control module may also include an input means for allowing the user to enter patient information, for example the identity of the patient, the type and concentration of the gas and dose of the gas to be administered to the patient, the patient's disease or condition to be treated by the gas or reason for treatment, gestational age of the patient and patient weight. The input means may include a keyboard integrated with the display. In one or more alternative embodiments, the input means may include a USB port or other port for the connection of an external keyboard or other input mechanism known in the art. The information entered via the input means is stored within the CPU memory.

Figure 2:
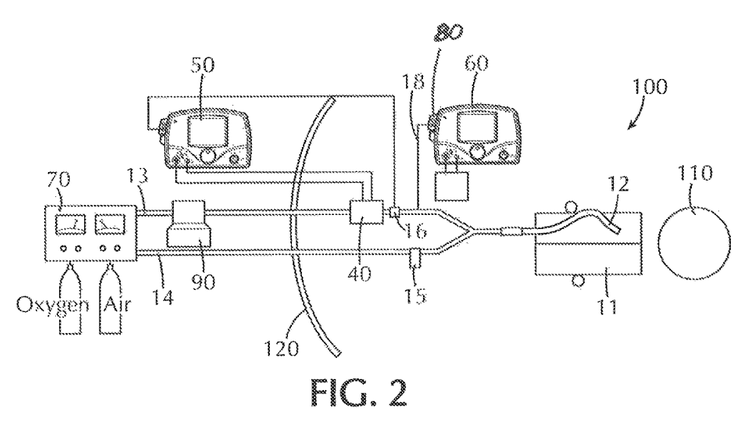
FIG. 2 is a schematic view of another embodiment of a nitric oxide delivery system of the present invention wherein the placement of injector module and injection tube is within an iso-gauss line with the nitric oxide injector module, injection tube and sampling Tee all being positioned just proximal to the patient WYE.

A second aspect of the present invention pertains to a gas delivery device to be utilized in an MRI suite that includes an injector module situated within the Iso-Gauss line of the gauss exclusion zone wherein said injector module is connected to a valve assembly in communication with a control module to control the delivery of gas from a gas source and ventilator to introduce the gas into the patient via a wye, nasal cannula, endotracheal tube, face mask or the like. In one or more embodiments, the injector module and injection port are both placed within the Iso-Gauss line just proximal to the patient WYE. This configuration was found to produce lower levels of $NO_2$ and NO levels within a desired range. As shown in FIG. 2, the placement of injector module and injection tube inside the iso-gauss line with the injector module, NO injection tube and sampling tee all being positioned just proximal to the patient WYE thus allowing for minimal contact duration between inspiratory oxygen and injected NO. In this embodiment, ventilator inspiratory flow is measured near the patient. In this embodiment, the injector module is composed of non-ferrous materials and functions predominantly free of signal interference produced by the strong magnetic field.

Another aspect of the present invention pertains to measurement of $NO_2$ from the sampling tube attached within the patient circuit to the sample Tee. Gas is sampled from this sampling tube within the patient circuit by a vacuum pump and routed to the previously described gas measurement bench. This bench measures $NO_2$ (as well as NO and O2) and the potential additional sampling transport delay caused by lengthened sampling tubing (consistent with placing the sampling Tee near the patient and away from the device) may cause erroneously high values of $NO_2$ to be reported by the measurement bench. Therefore, the invention includes the provision for an algorithm which corrects for this elevated level on $NO_2$ by taking into account the length of the tube and the resulting increased gas transit time.

Experimental Data

In order to determine the optimal configuration for an MRI compatible NO delivery device, a bench study was conducted using a ventilator and a TTL Lung Simulator to test three possible configurations of the MRI compatible NO delivery device. Ventilator and test lung settings were reflective of neonatal, pediatric and adult patient populations. The three configurations are discussed below.

As shown in FIG. 1, configuration #1 provides the injector module to be placed outside of the Iso-Gauss line with the gas injection inlet of the injector module capped. A sampling and gas injection tee were placed just proximal to the patient WYE.

As shown in FIG. 2, configuration #2 provides the injector module and injection port to both be placed within the Iso-Gauss line just proximal to the patient WYE.

Figure 3:
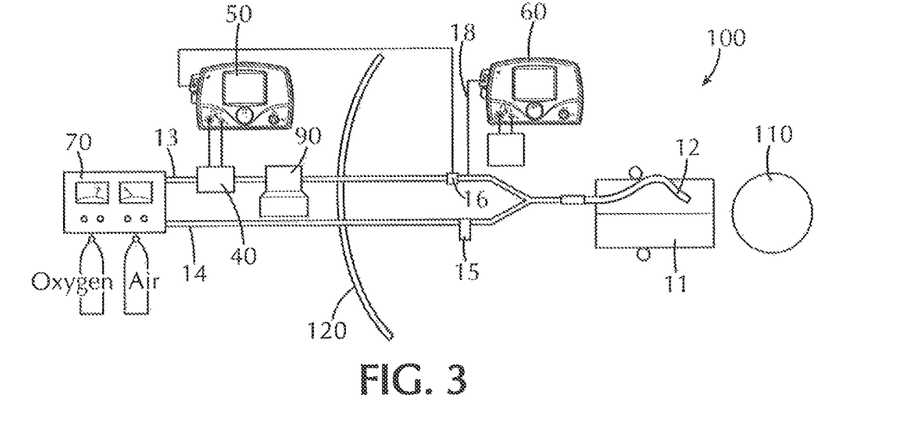
FIG. 3 is a schematic view of an embodiment of a nitric oxide delivery system wherein the nitric oxide injector module and injection port are placed beyond the iso-gauss line and the sampling Tee is placed just proximal to the patient WYE.
Figure 4:
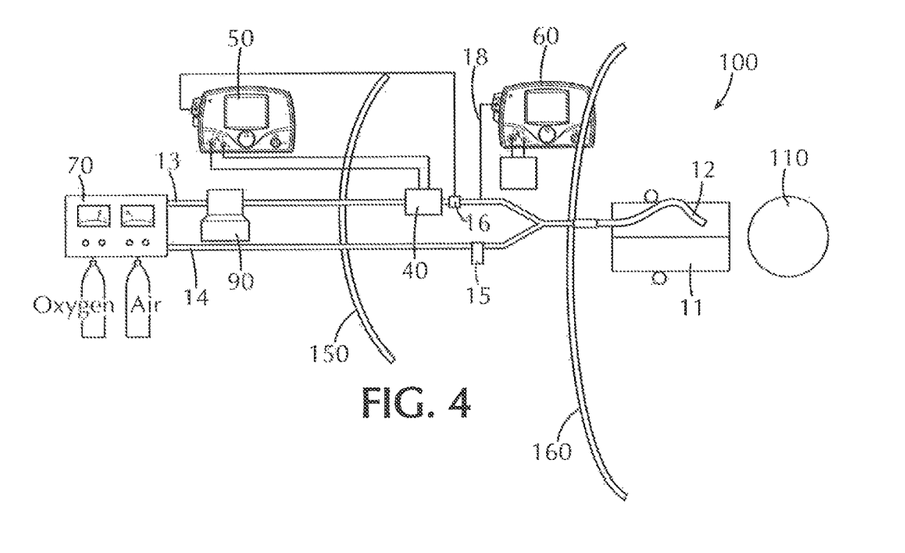
FIG. 4 is a schematic view of an embodiment of a nitric oxide delivery system wherein the nitric oxide injector module is placed within the low iso-gauss line and the sampling Tee is placed beyond the high iso-gauss line.

As shown in FIG. 3, configuration #3 provides the injector module and injection port to be placed beyond the Iso-Gauss (low flux safety) line of the MRI suite and the sampling Tee was placed just proximal to the patient WYE. FIG. 4 is a schematic view of an embodiment of a nitric oxide delivery system wherein the nitric oxide injector module is placed within the low iso-gauss line 150 (i.e. 5-200 gauss) and the sampling Tee is placed beyond the high iso-gauss line 160 (i.e. greater than 200 gauss).

The ventilator and test lung were set up to simulate a range of patients from neonatal to adult including the modeling of appropriately sized tidal volumes, breath rate, and representative pulmonary physiology. Tubing lengths including patient circuits, the sampling tube, and the injector tube were extended to represent the anticipated distance between the MRI imager and the iso-gauss line beyond which the NO delivery device is expected to be located during imaging. Sampled nitric oxide (NO) and nitrogen dioxide ($NO_2$) where then taken both from the unit under test (UUT) as well as from an ancillary unit. Inhaled Nitric Oxide (NO) delivery measurement accuracy, as well as in-circuit nitrogen dioxide ($NO_2$) production were measured just proximal to the patient WYE.

The NO delivery device performance was evaluated using a matrixed settings approach inclusive of the extended patient circuit and tubing lengths anticipated to be required in the MRI suite to allow for placement of the NO delivery device outside of the high magnetic flux environment produced by the imager. The settings for the ventilator and test lung are shown in Table 1 for all three patient populations (neonatal, pediatric, and adult).

TABLE 1

| Settings | Ventilator/Lung Settings | | |
|---|---|---|---|
| | Configuration 3 | Configuration 1 | Configuration 2 |
| | Neonatal | | |
| Tidal Volume (L/Min) | Run Term. Due to High $NO_2$ | 0.9 | 0.9 |
| Respiratory Rate (BPM) | — | 40 | 40 |
| $FIO_2$ | — | 0.21/0.6/1.0 | 0.21/0.6/1.0 |
| Inspiratory Time (sec) | — | 0.5 | 0.5 |

TABLE 1-continued

| Ventilator/Lung Settings | | | |
|---|---|---|---|
| Settings | Configuration 3 | Configuration 1 | Configuration 2 |
| Inspiratory Pause (sec) | — | 0 | 0 |
| Inspiratory Rise (sec) | — | 0.15 | 0.15 |
| Trigger Setting | — | Pres/20 | Pres/20 |
| PEEP (cmH$_2$O) | — | 0 | 0 |
| Patient Circuit Compliance | — | ON | ON |
| Circuit Diameter (mm) | — | 10 | 10 |
| Lung Comp (ml/cmH$_2$O) | — | 20 | 20 |
| Airway Resistance | — | Rp50 | Rp50 |
| Patient Circuit Length (ft) | — | 4/8/12 | 4/8/12 |
| Humidifier Volume (mL) | — | ~100 | ~100 |
| Water Trap in Circuit | — | NO | NO |
| Segment Lengths (A, B, C . . .) | — | 6, 6, 6, 6 | 6, 6, 6 |
| Pediatric | | | |
| Tidal Volume (L/Min) | 2.5/3.7 | 1.7/3.7 | 1.7/3.7 |
| Respiratory Rate (BPM) | 25 | 25 | 25 |
| FIO$_2$ | 0.21/0.6/1.0 | 0.21/0.6/1.0 | 0.21/0.6/1.0 |
| Inspiratory Time (sec) | 0.9 | 0.9 | 0.9 |
| Inspiratory Pause (sec) | 0 | 0 | 0 |
| Inspiratory Rise (sec) | 0.4 | 0.4 | 0.4 |
| Trigger Setting | Pres/20 | Pres/20 | Pres/20 |
| PEEP (cmH$_2$O) | 0 | 0 | 0 |
| Patient Circuit Compliance | ON | ON | ON |
| Circuit Diameter (mm) | 15 | 15 | 15 |
| Lung Comp (ml/cmH$_2$O) | 50 | 50 | 50 |
| Airway Resistance | Rp20 | Rp20 | Rp20 |
| Patient Circuit Length (ft) | 4/8/12 | 4/8/12 | 4/8/12 |
| Humidifier Volume (mL) | ~100 | ~100 | ~100 |
| Water Trap in Circuit | NO | NO | NO |
| Segment Lengths (A, B, C . . .) | 6, 6, 6, 6 | 6, 6, 6, 6 | 6, 6, 6 |
| Adult | | | |
| Tidal Volume (L/Min) | 4.8/6.0/6.6 | 4.8/6.6 | 4.8/6.6 |
| Respiratory Rate (BPM) | 12 | 12 | 12 |
| FIO$_2$ | 0.21/0.6/1.0 | 0.21/0.6/1.0 | 0.21/0.6/1.0 |
| Inspiratory Time (sec) | 1.0 | 1.0 | 1.0 |
| Inspiratory Pause (sec) | 0.0 | 0.0 | 0.0 |
| Inspiratory Rise (sec) | 0.4 | 0.4 | 0.4 |
| Trigger Setting | Pres/20 | Pres/20 | Pres/20 |
| PEEP (cmH$_2$O) | 0 | 0 | 0 |
| Patient Circuit Compliance | ON | ON | ON |
| Circuit Diameter (mm) | 22 | 22 | 22 |
| Lung Comp (ml/cmH$_2$O) | 80 | 80 | 80 |
| Airway Resistance | Rp5 | Rp5 | Rp5 |
| Patient Circuit Length (ft) | 6/12/18 | 6/12/18 | 6/12/18 |
| Humidifier Volume (mL) | 280 | 280 | 280 |
| Water Trap in Circuit | YES | YES | YES |
| Segment Lengths (A, B, C . . .) | 6, 6, 6, 6 | 6, 6, 6, 6 | 6, 6, 6 |

The ventilator settings for typical adult, pediatric and neonatal patients were taken from the ventilation nomogram found in a paper by Radford et al. (New England J Med. 251:877, 1954) 1 incorporated by reference in its entirety. All testing was performed on high and zero value calibrated NO delivery devices. Testing was conducted using one, two and three lengths of patient circuit tubing to simulate the anticipated placement of the ventilator well clear of the high flux generating bore of the MRI machine, e.g. beyond the iso-gauss line. In addition, both the sample and injector tubes were extended to twice their current length using a straight through barbed connector (Qosina P/N 11689, Edgewood, N.Y.) connected to snipped ends of two injector tubes effectively doubling its length, and by snipping and bridging the snipped ends of the sampling tube by inserting them into a ⅛" ID, 10 foot segment of silicone tubing (Qosina P/N T2013, Edgewood, N.Y.). The ventilator was taken through a full pre-use check out after each change in the length of patient circuit tubing applied and "patient circuit compliance compensation" (PCCC) was enabled for each patient circuit configuration. Each configuration tested included a Fisher and Paykel MR850 humidifier with an MR290 humidification chamber filled to allow for either 280 ml (filled to the water line) or ~100 ml of compressible volume for adults and pediatrics/neonate settings respectively. For test Configuration #1, the injector module injection port was capped by clamping a spare injection tube connected to the injector module. All testing was monitored by using the unit under test's own NO and NO$_2$ gas sensors. A redundant "measuring" NO delivery device was connected to all three test configurations for a "sanity check" on the quality of data being recorded from the unit under test. Finally, data collection for each individual setting followed a settling time sufficient to ensure reading stability.

Results

NO Accuracy/NO$_2$ Production. Results of the data collection for the three configurations tested are shown in Tables 2, 3 and 4 and show the measured NO and NO$_2$ levels for each test configuration based on the settings in Table 1. Table 2 shows the results of running Configuration #3. Testing of Configuration #3 was terminated following adult and pediatric settings due to high measured NO$_2$. Results in Table 2 are shown for one, two and three lengths (4, 8 and 12 ft) of patient circuit tubing.

TABLE 2

| | NO (ppm)/NO$_2$ (ppm) | | | | | | | | |
|---|---|---|---|---|---|---|---|---|---|
| FIO$_2$ | 20 | | | 50 | | | 80 | | |

| $V_E$ = 1.7 L/min (pediatric) | | | | | | | | | |
|---|---|---|---|---|---|---|---|---|---|
| | 4 ft | 8 ft | 12 ft | 4 ft | 8 ft | 12 ft | 4 ft | 8 ft | 12 ft |
| 0.21 | 19/0.1 | 19/0.1 | 20/0.1 | 51/0.3 | 51/0.3 | 49/0.3 | 80/0.5 | 81/0.6 | 81/0.6 |
| 0.6 | 20/0.2 | 19/0.2 | 21/0.2 | 51/0.5 | 52/0.7 | 49/0.7 | 80/1.2 | 79/1.4 | 82/1.5 |
| 1.0 | 20/0.2 | 20/0.2 | 20/0.2 | 51/0.8 | 51/1.0 | 50/1.1 | 82/2.0 | 82/2.3 | 82/2.4 |

| $V_E$ = 3.7 L/min (pediatric) | | | | | | | | | |
|---|---|---|---|---|---|---|---|---|---|
| | 4 ft | 8 ft | 12 ft | 4 ft | 8 ft | 12 ft | 4 ft | 8 ft | 12 ft |
| 0.21 | 20/0.1 | 19/0.1 | 19/0.1 | 51/0.3 | 51/0.3 | 50/0.3 | 81/0.5 | 81/0.6 | 80/0.6 |
| 0.6 | 19/0.1 | 20/0.2 | 19/0.1 | 51/0.5 | 51/0.5 | 51/0.6 | 81/1.1 | 81/1.2 | 82/1.3 |
| 1.0 | 19/0.2 | 20/0.2 | 21/0.2 | 51/0.9 | 51/0.9 | 52/1.0 | 81/1.4 | 82/1.9 | 82/2.1 |

| $V_E$ = 4.8 L/min (adult) | | | | | | | | | |
|---|---|---|---|---|---|---|---|---|---|
| | 6 ft | 12 ft | 18 ft | 6 ft | 12 ft | 18 ft | 6 ft | 12 ft | 18 ft |
| 0.21 | 20/-.1 | 21/0.0 | 19/0.0 | 50/0.0 | 51/0.0 | 51/0.1 | 81/0.1 | 81/0.4 | 81/0.5 |
| 0.6 | 21/0.1 | 20/0.0 | 20/0.2 | 52/0.6 | 52/0.6 | 52/1.0 | 81/1.1 | 87/1.1 | 88/1.1 |
| 1.0 | 19/0.2 | 20/0.2 | 19/0.2 | 56/1.3 | 52/1.3 | 51/1.6 | 85/2.6 | 87/3.1 | 82/4.0 |

| $V_E$ = 6.6 L/min (adult) | | | | | | | | | |
|---|---|---|---|---|---|---|---|---|---|
| | 6 ft | 12 ft | 18 ft | 6 ft | 12 ft | 18 ft | 6 ft | 12 ft | 18 ft |
| 0.21 | 18/0.0 | 19/0.0 | 19/0.0 | 50/0.1 | 51/0.1 | 51/0.1 | 81/0.2 | 81/0.3 | 80/0.4 |
| 0.6 | 20/0.1 | 19/0.0 | 21/0.1 | 51/0.5 | 51/0.6 | 52/0.9 | 80/1.0 | 81/1.7 | 80/1.9 |
| 1.0 | 20/0.2 | 23/0.2 | 20/0.2 | 50/1.0 | 50/1.1 | 51/1.4 | 88/2.2 | 81/2.6 | 80/3.3 |

Table 3 shows the results of running Configuration #1. Results are shown for one, two and three lengths (4, 8 and 12 ft and 6, 12 and 18 ft) of patient circuit tubing.

TABLE 3

| | NO (ppm)/NO$_2$ (ppm) | | | | | | | | |
|---|---|---|---|---|---|---|---|---|---|
| FIO$_2$ | 20 | | | 50 | | | 80 | | |

| $V_E$ = 0.9 L/min (neonatal) | | | | | | | | | |
|---|---|---|---|---|---|---|---|---|---|
| | 4 ft | 8 ft | 12 ft | 4 ft | 8 ft | 12 ft | 4 ft | 8 ft | 12 ft |
| 0.21 | 19/0.0 | 17/0.0 | 16/0.0 | 47/0.3 | 47/0.1 | 49/0.2 | 78/0.2 | 78/0.3 | 77/0.3 |
| 0.6 | 18/0.1 | 18/0.1 | 17/0.1 | 48/0.4 | 47/0.3 | 49/0.4 | 78/0.8 | 79/0.8 | 77/0.8 |
| 1.0 | 21/0.1 | 20/0.1 | 23/0.2 | 52/0.8 | 51/0.7 | 52/0.8 | 77/1.5 | 79/1.5 | 75/1.5 |

| $V_E$ = 2.5 L/min (pediatric) | | | | | | | | | |
|---|---|---|---|---|---|---|---|---|---|
| | 4 ft | 8 ft | 12 ft | 4 ft | 8 ft | 12 ft | 4 ft | 8 ft | 12 ft |
| 0.21 | 19/0.1 | 18/0.0 | 20/0.0 | 48/0.1 | 48/0.1 | 46/0.1 | 79/0.1 | 78/0.2 | 77/0.2 |
| 0.6 | 24/0.0 | 18/0.0 | 19/0.0 | 50/0.2 | 51/0.3 | 44/0.2 | 78/0.4 | 76/0.6 | 76/0.5 |
| 1.0 | 20/0.0 | 19/0.1 | 20/0.1 | 49/0.4 | 52/0.4 | 45/0.4 | 81/1.2 | 80/1.3 | 82/1.3 |

| $V_E$ = 3.7 L/min (pediatric) | | | | | | | | | |
|---|---|---|---|---|---|---|---|---|---|
| | 4 ft | 8 ft | 12 ft | 4 ft | 8 ft | 12 ft | 4 ft | 8 ft | 12 ft |
| 0.21 | 18/0.0 | 17/0.0 | 19/0.0 | 49/0.1 | 45/0.1 | 45/0.1 | 80/0.2 | 81/0.2 | 80/0.2 |
| 0.6 | 17/0.0 | 18/0.0 | 18/0.0 | 52/0.3 | 51/0.3 | 48/0.3 | 81/0.6 | 82/0.7 | 85/0.7 |
| 1.0 | 18/0.1 | 18/0.1 | 17/0.1 | 51/0.4 | 50/0.4 | 50/0.5 | 79/1.2 | 79/1.2 | 82/1.4 |

TABLE 3-continued

| | NO (ppm)/NO₂ (ppm) | | | | | | | | |
|---|---|---|---|---|---|---|---|---|---|
| FIO₂ | 20 | | | 50 | | | 80 | | |

$V_E$ = 4.8 L/min (adult)

| | 6 ft | 12 ft | 18 ft | 6 ft | 12 ft | 18 ft | 6 ft | 12 ft | 18 ft |
|---|---|---|---|---|---|---|---|---|---|
| 0.21 | 21/0.0 | 22/0.1 | 22/0.0 | 52/0.0 | 50/−0.1 | 49/0.1 | 83/0.2 | 83/0.2 | 79/0.3 |
| 0.6 | 20/0.0 | 21/0.0 | 22/0.0 | 50/0.2 | 52/0.2 | 51/0.2 | 83/0.7 | 78/0.7 | 80/0.8 |
| 1.0 | 22/0.1 | 22/0.0 | 24/0.0 | 51/0.4 | 53/0.5 | 52/0.4 | 85/1.2 | 83/1.3 | 77/1.3 |

$V_E$ = 6 L/min (adult)

| | 6 ft | 12 ft | 18 ft | 6 ft | 12 ft | 18 ft | 6 ft | 12 ft | 18 ft |
|---|---|---|---|---|---|---|---|---|---|
| 0.21 | 22/0.0 | 22/0.1 | 23/0.0 | 51/0.0 | 51/0.0 | 51/0.0 | 84/0.2 | 83/0.2 | 80/0.1 |
| 0.6 | 23/0.0 | 22/0.0 | 23/0.0 | 50/0.2 | 53/0.2 | 52/0.2 | 84/0.7 | 84/0.7 | 81/0.6 |
| 1.0 | 22/0.0 | 22/0.0 | 24/0.1 | 53/0.5 | 52/0.5 | 52/0.5 | 88/1.1 | 82/1.2 | 80/1.1 |

$V_E$ = 6.6 L/min (adult)

| | 6 ft | 12 ft | 18 ft | 6 ft | 12 ft | 18 ft | 6 ft | 12 ft | 18 ft |
|---|---|---|---|---|---|---|---|---|---|
| 0.21 | 21/0.0 | 21/0.0 | 23/0.0 | 49/0.1 | 52/−0.1 | 53/0.1 | 85/0.2 | 77/0.3 | 80/0.2 |
| 0.6 | 23/0.0 | 22/0.0 | 24/0.0 | 54/0.2 | 54/0.2 | 53/0.2 | 87/0.9 | 84/0.7 | 79/0.6 |
| 1.0 | 21/0.0 | 23/0.1 | 24/0.0 | 53/0.5 | 54/0.5 | 54/0.5 | 87/1.2 | 82/1.2 | 81/1.1 |

Table 4 shows the results of running Configuration #2. Results are shown for one, two and three lengths (4, 8 and 12 ft and 6, 12 and 18 ft) of patient circuit tubing. NO results outside of spec are indicated in bold.

| | NO (ppm)/NO₂ (ppm) | | | | | | | | |
|---|---|---|---|---|---|---|---|---|---|
| FIO₂ | 20 | | | 50 | | | 80 | | |

$V_E$ = 0.9 L/min (neonatal)

| | 4 ft | 8 ft | 12 ft | 4 ft | 8 ft | 12 ft | 4 ft | 8 ft | 12 ft |
|---|---|---|---|---|---|---|---|---|---|
| 0.21 | 19/0.0 | 20/0.0 | 19/0.0 | 51/0.2 | 48/0.1 | 51/0.1 | 81/0.3 | 80/0.3 | 83/0.4 |
| 0.6 | 18/0.1 | 20/0.1 | 19/0.1 | 50/0.5 | 46/0.4 | 51/0.4 | 95/0.8 | 85/1.0 | 78/1.0 |
| 1.0 | 20/0.1 | 20/0.1 | 22/0.1 | 50/0.8 | 48/0.7 | 51/0.7 | 80/1.5 | 81/1.6 | 80/1.6 |

$V_E$ = 2.5 L/min (pediatric)

| | 4 ft | 8 ft | 12 ft | 4 ft | 8 ft | 12 ft | 4 ft | 8 ft | 12 ft |
|---|---|---|---|---|---|---|---|---|---|
| 0.21 | 22/0.1 | 22/0.0 | 22/0.1 | 53/0.2 | 58/0.1 | 54/0.1 | 92/0.4 | 92/0.3 | 91/0.3 |
| 0.6 | 23/0.1 | 20/0.0 | 22/0.0 | 56/0.5 | 55/0.5 | 56/0.4 | 91/1.3 | 91/1.3 | 91/1.2 |
| 1.0 | 23/0.2 | 20/0.1 | 22/0.0 | 58/0.6 | 57/0.5 | 56/0.5 | 91/1.7 | 90/1.7 | 92/1.7 |

$V_E$ = 3.7 L/min (pediatric)

| | 4 ft | 8 ft | 12 ft | 4 ft | 8 ft | 12 ft | 4 ft | 8 ft | 12 ft |
|---|---|---|---|---|---|---|---|---|---|
| 0.21 | 20/0.1 | 22/0.1 | 21/0.0 | 57/0.2 | 55/0.1 | 56/0.1 | 91/0.4 | 91/0.3 | 89/0.3 |
| 0.6 | 23/0.1 | 22/0.1 | 22/0.0 | 57/0.5 | 57/0.4 | 55/0.4 | 93/1.2 | 91/1.2 | 91/1.2 |
| 1.0 | 23/0.2 | 20/0.2 | 23/0.1 | 57/0.8 | 56/0.7 | 56/0.6 | 90/1.6 | 93/1.6 | 90/1.6 |

$V_E$ = 4.8 L/min (adult)

| | 6 ft | 12 ft | 18 ft | 6 ft | 12 ft | 18 ft | 6 ft | 12 ft | 18 ft |
|---|---|---|---|---|---|---|---|---|---|
| 0.21 | 21/0.0 | 21/0.0 | 22/0.1 | 55/0.1 | 52/0.2 | 54/0.2 | 87/0.5 | 87/0.4 | 88/0.4 |
| 0.6 | 23/0.0 | 22/0.1 | 24/0.0 | 57/0.4 | 56/0.4 | 53/0.4 | 83/1.1 | 87/1.1 | 88/1.1 |
| 1.0 | 22/0.2 | 24/0.2 | 25/0.2 | 57/0.8 | 56/0.7 | 57/0.7 | 85/1.7 | 88/1.7 | 91/1.8 |

$V_E$ = 6 L/min (adult)

| | 6 ft | 12 ft | 18 ft | 6 ft | 12 ft | 18 ft | 6 ft | 12 ft | 18 ft |
|---|---|---|---|---|---|---|---|---|---|
| 0.21 | 21/0.0 | 22/0.1 | 23/0.0 | 55/0.1 | 57/0.2 | 57/0.2 | 87/0.5 | 88/0.4 | 88/0.4 |
| 0.6 | 22/0.0 | 23/0.1 | 23/0.1 | 56/0.4 | 57/0.5 | 57/0.5 | 88/1.1 | 88/1.1 | 90/1.1 |
| 1.0 | 22/0.1 | 23/0.1 | 24/0.2 | 57/0.7 | 56/0.6 | 54/0.7 | 87/1.7 | 88/1.7 | 88/1.7 |

-continued

| | NO (ppm)/NO$_2$ (ppm) | | | | | | | | |
|---|---|---|---|---|---|---|---|---|---|
| FIO$_2$ | 20 | | | 50 | | | 80 | | |
| | $V_E$ = 6.6 L/min (adult) | | | | | | | | |
| | 6 ft | 12 ft | 18 ft | 6 ft | 12 ft | 18 ft | 6 ft | 12 ft | 18 ft |
| 0.21 | 22/0.0 | 22/0.0 | 23/0.1 | 54/0.1 | 51/0.2 | 52/0.2 | 88/0.5 | 88/0.5 | 90/0.5 |
| 0.6 | 21/0.0 | 24/0.1 | 24/0.1 | 56/0.4 | 54/0.5 | 55/0.5 | 88/1.2 | 92/1.2 | 92/1.2 |
| 1.0 | 23/0.1 | 24/0.2 | 25/0.2 | 55/0.7 | 54/0.7 | 55/0.7 | 86/1.6 | 89/1.7 | 90/1.8 |

The results were evaluated based on the accuracy of delivered NO (i.e. does the NO delivery meet specification) and based on the amount of NO$_2$ produced (i.e. is the NO$_2$ production above acceptable levels). Results are reported for each patient circuit tubing length investigated. Patient circuit tubing was ganged together in single, double and triple lengths to simulate the anticipated distance between the NO delivery device and the patient in an MRI setting. Configurations #1 and 2 were found to deliver lower levels of NO$_2$ (compared to Configuration #3) while delivering NO within specification. Configuration #3 was found to produce high levels of NO$_2$. Testing of Configuration #3 was aborted after both Adult and Pediatric patient settings were investigated.

Pressure Vs. Flow Triggering

The effect of changing from the standard pressure triggering setting to a flow triggering setting was investigated. Table 5 shows the settings for Flow Triggering Test. Flow triggering is achieved on ICU ventilators with a low patient circuit bias or background flow (not present with pressure triggering) thus, potentially changing the residence or contact time between oxygen and NO (which produces NO$_2$ due to time/concentration dependent oxidation of NO).

TABLE 5

| Ventilator/Lung Settings | |
|---|---|
| Settings | Configuration 1 |
| NO Delivery Setting (ppm) | 80 |
| Tidal Volume (L/Min) | 3.7 |
| Respiratory Rate (BPM) | 25 |
| FIO$_2$ | 1.0 |
| Inspiratory Time (sec) | 0.9 |
| Inspiratory Pause (sec) | 0 |
| Inspiratory Rise (sec) | 0.4 |
| Trigger Setting | Pres/20/FT 1, 5, 10 |
| PEEP (cmH$_2$O) | 0 |
| Patient Circuit Compliance | ON |
| Circuit Diameter (mm) | 15 |
| Lung Comp (ml/cmH$_2$O) | 50 |
| Airway Resistance | Rp20 |
| Patient Circuit Length (ft) | 12 |
| Humidifier Volume (mL) | 100 |
| Water Trap in Circuit | NO |
| Segment Lengths (A, B, C . . .) | 6, 6, 6, 6 |

Increased Sampling Tube Length

The effect of doubling the length of the sampling tubing (from 10 to 20 ft) to simulate NO Delivery device placement at an increased distance from the MRI machine was investigated. Table 6 shows the settings for the sampling tube shortening test.

TABLE 6

| Ventilator/Lung Settings | |
|---|---|
| Settings | Configuration 1 |
| NO Delivery Setting (ppm) | 80 |
| Tidal Volume (L/Min) | 2.5, 3.7 |
| Respiratory Rate (BPM) | 25 |
| FIO$_2$ | 1.0 |
| Inspiratory Time (sec) | 0.9 |
| Inspiratory Pause (sec) | 0 |
| Inspiratory Rise (sec) | 0.4 |
| Trigger Setting | Pres/20 |
| PEEP (cmH$_2$O) | 0 |
| Patient Circuit Compliance | ON |
| Circuit Diameter (mm) | 15 |
| Lung Comp (ml/cmH$_2$O) | 50 |
| Airway Resistance | Rp20 |
| Patient Circuit Length (ft) | 12 |
| Humidifier Volume (mL) | 100 |
| Water Trap in Circuit | NO |
| Segment Lengths (A, B, C . . .) | 6, 6, 6, 6 |

As shown in Table 7, the increased residence time of oxygen and NO within the sample tube of increased length is sufficient to lead to increased NO$_2$ production as measured at the NO$_2$ sensor of the NO delivery device.

TABLE 7

| Ventilator/Lung Settings | |
|---|---|
| Settings (Short = 10 ft, Long = 20 ft) | Measured NO$_2$ |
| Short Tube @ TV = 2.5 | 1.0 |
| Long Tube @ TV = 2.5 | 1.6 |
| Short Tube @ TV = 3.7 | 0.8 |
| Long Tube @ TV = 3.7 | 1.5 |

The effect of doubling the length of the Injector tubing (from 6 to 12 ft) to simulate the NO delivery device being placed at an increased distance from the MRI machine was investigated. The increased distance that the N$_2$/NO drug (gas) blend must travel to the patient circuit may potentially lead to a time lag in the delivery system producing ventilator/NO delivery device disynchrony, a condition in which the delivered waveform from the NO delivery device lags significantly behind the delivered flow waveform from the ventilator. Table 8 shows the settings for the injector tube shortening test.

TABLE 8

Ventilator/Lung Settings

| Settings | Configuration 1 |
| --- | --- |
| NO Delivery Setting (ppm) | 80 |
| Tidal Volume (L/Min) | 2.5, 3.7 |
| Respiratory Rate (BPM) | 25 |
| $FIO_2$ | 1.0 |
| Inspiratory Time (sec) | 0.9 |
| Inspiratory Pause (sec) | 0 |
| Inspiratory Rise (sec) | 0.4 |
| Trigger Setting | Pres/20 |
| PEEP ($cmH_2O$) | 0 |
| Patient Circuit Compliance | ON |
| Circuit Diameter (mm) | 15 |
| Lung Comp ($ml/cmH_2O$) | 50 |
| Airway Resistance | Rp20 |
| Patient Circuit Length (ft) | 12 |
| Humidifier Volume (mL) | 100 |
| Water Trap in Circuit | NO |
| Segment Lengths (A, B, C . . .) | 6, 6, 6, 6 |

As shown in Table 8, the effect of doubling the length of the sampling tubing has a significant impact on the measured $NO_2$. The longer tube results in longer gas transit time from the sampling Tee in the patient circuit to the $NO_2$ sensor located inside the NO delivery device. The longer transit time is due to the fact that the sample pump does not change speeds or vacuum flow rate when the double length sampling tube is attached. Therefore an approximate "times two" multiplier on gas sampling transit time is a reasonable assumption. This increased transit time allows additional time for oxygen to oxidize the NO into $NO_2$. Table 8 shows that the effect almost doubles the measured concentration of $NO_2$. Thus, the MRI compatible NO delivery device should likely include an $NO_2$ correction algorithm in which the measured $FIO_2$, the measured NO concentration and potentially other critical variables are used to estimate the over-measurement of $NO_2$ for later correction in the display.

As shown in Table 9, ventilator/NO delivery device disynchrony could potentially produce errant NO readings at the NO delivery device.

TABLE 9

Ventilator/Lung Settings

| Settings (Short = 10 ft, Long = 20 ft) | Measured NO |
| --- | --- |
| Short Tube @ TV = 2.5 | 81 |
| Long Tube @ TV = 2.5 | 83 |
| Short Tube @ TV = 3.7 | 81 |
| Long Tube @ TV = 3.7 | 82 |

NO Accuracy/$NO_2$ Production

Results of the extensive testing clearly show that Configuration #3, in which the injection of NO occurs well upstream of the sampling of gas for measurement, produces high levels of $NO_2$. This high $NO_2$ production is assumed to be the result of longer contact time between the oxygen in the inspiratory stream of the ventilator and the NO (NO/N2 mix) gas as delivered by the NO delivery device. Settings in which a high $FIO_2$ and high NO concentration were employed resulted in the highest measured values of $NO_2$. A value of 4 ppm was measured which is well above the NIOSH (8 hour time weighted average) guidelines of <1 ppm $NO_2$ exposure. The lengthened sampling line of Configuration #3 was found to produce higher measured $NO_2$ levels than those measured during normal use of the NO delivery device. Nonetheless, concentrations of 4 ppm measured $NO_2$ are still comparatively high relative to concentrations measured using Configurations #1 and #2, and for this reason, Configuration #3 can be eliminated as a potential configuration for implementation of a commercial MRI option. Configurations #1 and #2 both involve injection of NO and sampling of the gas mix just proximal to the patient WYE. Since both of these configurations do not produce a significant contact duration between inspiratory oxygen and injected NO, the measured levels of $NO_2$ in Configurations #1 and #2 were much lower than that seen in Configuration #3. The difference between Configurations #1 and #2 is that Configuration #1 measures ventilator inspiratory flow near the ventilator while Configuration #2 measures ventilator inspiratory flow near the patient. As a result, the injector module in Configuration #2 would be well within the high magnetic flux field of the MRI imager. This could potentially be problematic both relative to the accuracy of the flow signals transmitted from the injector module to the NO delivery device, as well as potentially problematic to the image clarity of the MRI machine itself for which images can become distorted from magnetically susceptible materials in close proximity to the imaging field. The benefit, however, of Configuration #2 is that the injector module of Configuration 2 is designed to be non-ferrous to shield or improve circuit performance. Thus, Configurations #1 and #2 both provide good performance relative to NO delivery accuracy and $NO_2$ production for implementation in an MRI compatible device.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and device of the present invention without departing from the spirit and scope of the invention. Thus, it is intended that the present invention include modifications and variations that are within the scope of the appended claims and their equivalents.

What is claimed is:

1. A nitric oxide delivery system for providing inhaled nitric oxide (iNO) to a patient situated in an MRI suite, the nitric oxide delivery system comprising:
   a patient connector;
   a source of nitric oxide gas;
   a length of an iNO delivery tube;
   a source of breathing gas;
   a monitoring control circuit;
   a delivery control circuit;
   a signal processor including a corrective signal processing algorithm comprising determining an inverse of the distortion transfer function produced by the length of iNO delivery tube; determining a ventilator flow profile of individual breaths performed on a continuing basis during ventilation; convolving the inverse of a distortion transfer function with a predicted breath flow profile; and verifying a consistent ventilator flow profile; and an injector module fluidly connected to the source of nitric oxide, the source of breathing gas and the delivery control circuit; said injector module being located outside an iso-gauss safety line.

2. The nitric oxide delivery system of claim 1, wherein said patient connector is a wye.

3. The nitric oxide delivery system of claim 2, wherein said wye comprises an inspiratory limb and an expiratory limb.

4. The nitric oxide delivery system of claim 3, wherein a sampling tee and a gas injection tee are inserted into the inspiratory limb just proximal to the patient wye, and ventilator/waveform disynchrony is introduced by gas transport delays within the length of the iNO delivery tube connected to the gas injection tee.

5. The nitric oxide delivery system of claim 1, wherein the iNO delivery tube comprises tubing materials and or coatings which minimize oxygen ingress, thereby limiting $NO_2$ formation.

6. The nitric oxide delivery system of claim 4, wherein the length of iNO delivery tube connected to the gas injection tee minimizes both temporal flow distortion effects and $NO_2$ buildup effects in the iNO delivery tube.

7. The nitric oxide delivery system of claim 1, wherein the corrective signal processing algorithm removes distortion and delay caused by the length of iNO delivery tube.

8. The nitric oxide delivery system of claim 1, wherein the monitoring control circuit comprises a monitor CPU, a zero valve, sample pump, sampling port, sample flow sensor, and gas sampling bench.

9. The nitric oxide delivery system of claim 1, wherein the delivery control circuit comprises pressure transducer, a backup on/off switch, a pressure regulator, shutoff valve, a proportional control valve, and flow sensor.

10. The nitric oxide delivery system of claim 1, wherein the source of breathing gas is a mechanical ventilator.

11. The nitric oxide delivery system of claim 1, further including an alarm system operable by a signal from the signal processor indicative of a pre-determined concentration of NO.

12. The nitric oxide delivery system of claim 1 further comprising a display that provides an on-screen setup guide for use in the MRI suite.

13. The nitric oxide delivery system of claim 9, wherein the flow sensor is a thermal mass flowmeter, pneumotach, hot wire anemometer, thermal flow sensor, variable orifice, thermal time-of-flight, or rotating vane.

14. A nitric oxide delivery system for providing inhaled nitric oxide (iNO) to a patient situated in an MRI suite, the nitric oxide delivery system comprising: a patient connector; a source of nitric oxide gas; a length of an iNO delivery tube; a source of breathing gas; a monitoring control circuit; a delivery control circuit; a signal processor including a corrective signal processing algorithm comprising determining an inverse of a distortion transfer function produced by the length of iNO delivery tube; determining a ventilator flow profile of individual breaths performed on a continuing basis during ventilation; convolving the inverse of the distortion transfer function with a predicted breath flow profile; and verifying a consistent ventilator flow profile; and an injector module fluidly connected to the source of nitric oxide, the source of breathing gas and the delivery control circuit; said injector module being located inside an iso-gauss safety line.

15. The nitric oxide delivery system of claim 14, wherein the injector module is made of non-ferrous materials.

16. The nitric oxide delivery system of claim 14, wherein the injector module is located upstream from a humidifier.

17. The nitric oxide delivery system of claim 14, wherein the delivery system is made of non-ferrous materials.

18. The nitric oxide delivery system of claim 14, further comprising a display that provides an on-screen setup guide for use in the MRI suite.

* * * * *